US007905847B2

(12) United States Patent
Barker

(10) Patent No.: US 7,905,847 B2
(45) Date of Patent: *Mar. 15, 2011

(54) DEVICE FOR PROTECTING WOUNDS ON LIMBS

(75) Inventor: Stephen George Edward Barker, London (GB)

(73) Assignee: Ark Therapeutics Limited, London (GB)

(*) Notice: Subject to any disclaimer, the term of this patent is extended or adjusted under 35 U.S.C. 154(b) by 114 days.

This patent is subject to a terminal disclaimer.

(21) Appl. No.: 12/129,134

(22) Filed: May 29, 2008

(65) Prior Publication Data

US 2008/0228122 A1 Sep. 18, 2008

Related U.S. Application Data

(63) Continuation of application No. 11/265,941, filed on Nov. 3, 2005, which is a continuation-in-part of application No. 09/889,940, filed as application No. PCT/GB00/00208 on Jan. 26, 2000, now Pat. No. 6,982,358.

(30) Foreign Application Priority Data

Jan. 26, 1999 (GB) .................................. 9901711.3
Jul. 23, 1999 (GB) .................................. 9917443.5
Jul. 23, 1999 (GB) .................................. 9917445.0

(51) Int. Cl.
*A61F 5/00* (2006.01)
*A61F 13/00* (2006.01)

(52) U.S. Cl. .................. 602/3; 602/60; 602/62; 602/63

(58) Field of Classification Search .......... 602/3, 60–64, 602/40–43; 128/846, 888, 889; 206/204
See application file for complete search history.

(56) References Cited

U.S. PATENT DOCUMENTS

| 2,690,415 | A | | 9/1954 | Shuler | |
| 3,476,109 | A | * | 11/1969 | Hurney | 602/1 |
| 3,477,427 | A | | 11/1969 | Lapidus | |
| 3,741,203 | A | * | 6/1973 | Liman | 602/3 |
| 4,178,924 | A | | 12/1979 | Baxter | |
| 4,415,087 | A | * | 11/1983 | Clayton et al. | 383/211 |
| 4,619,361 | A | * | 10/1986 | Thomas, Jr. | 206/204 |
| 4,649,910 | A | | 3/1987 | Poenitsch | |
| 4,742,908 | A | * | 5/1988 | Thomas et al. | 206/204 |
| 4,815,590 | A | * | 3/1989 | Peppiatt et al. | 206/204 |

(Continued)

FOREIGN PATENT DOCUMENTS

DE 298 16 198 U1 9/1998

(Continued)

OTHER PUBLICATIONS

"Healing Difficult Wounds" Advertisement by THBO (Topical Hyperbaric Oxygen Therapy): www.thbo.com pp. 1-3 and 1-4, copyright 1996 to date.

*Primary Examiner* — Kim M Lewis
(74) *Attorney, Agent, or Firm* — Saliwanchik, Lloyd & Eisenschenk

(57) ABSTRACT

A device which comprises an enclosure of a plastics material, having an opening at an end thereof with fastening means to enable the opening to be closed around a limb or stump with an affected part contained within the enclosure, and including a fluid-absorbent material within the enclosure. The device is particularly suitable for use in the treatment of leg ulcers.

6 Claims, 4 Drawing Sheets

U.S. PATENT DOCUMENTS

| | | |
|---|---|---|
| 5,342,286 A | 8/1994 | Kelly et al. |
| 5,395,302 A | 3/1995 | Botha et al. |
| 5,403,265 A | 4/1995 | Berguer et al. |
| 5,404,999 A * | 4/1995 | Bednar .................. 206/204 |
| 5,549,587 A * | 8/1996 | Norton .................. 604/333 |
| 5,662,625 A | 9/1997 | Westwood |
| 5,711,760 A | 1/1998 | Ibrahim et al. |
| 5,720,713 A * | 2/1998 | Hutchison .................. 602/3 |
| 5,817,038 A | 10/1998 | Orange et al. |
| 5,914,125 A * | 6/1999 | Andrews et al. .............. 424/443 |
| 5,919,180 A | 7/1999 | Raimondo |
| 6,077,526 A | 6/2000 | Scully et al. |
| 6,089,367 A * | 7/2000 | Anderson et al. ............. 206/204 |
| 6,664,434 B2 * | 12/2003 | Cominsky ..................... 602/41 |
| 6,982,358 B1 * | 1/2006 | Barker .......................... 602/42 |

FOREIGN PATENT DOCUMENTS

| | | |
|---|---|---|
| EP | 0 966 892 A2 | 12/1999 |
| GB | 2283006 A * | 4/1995 |

\* cited by examiner

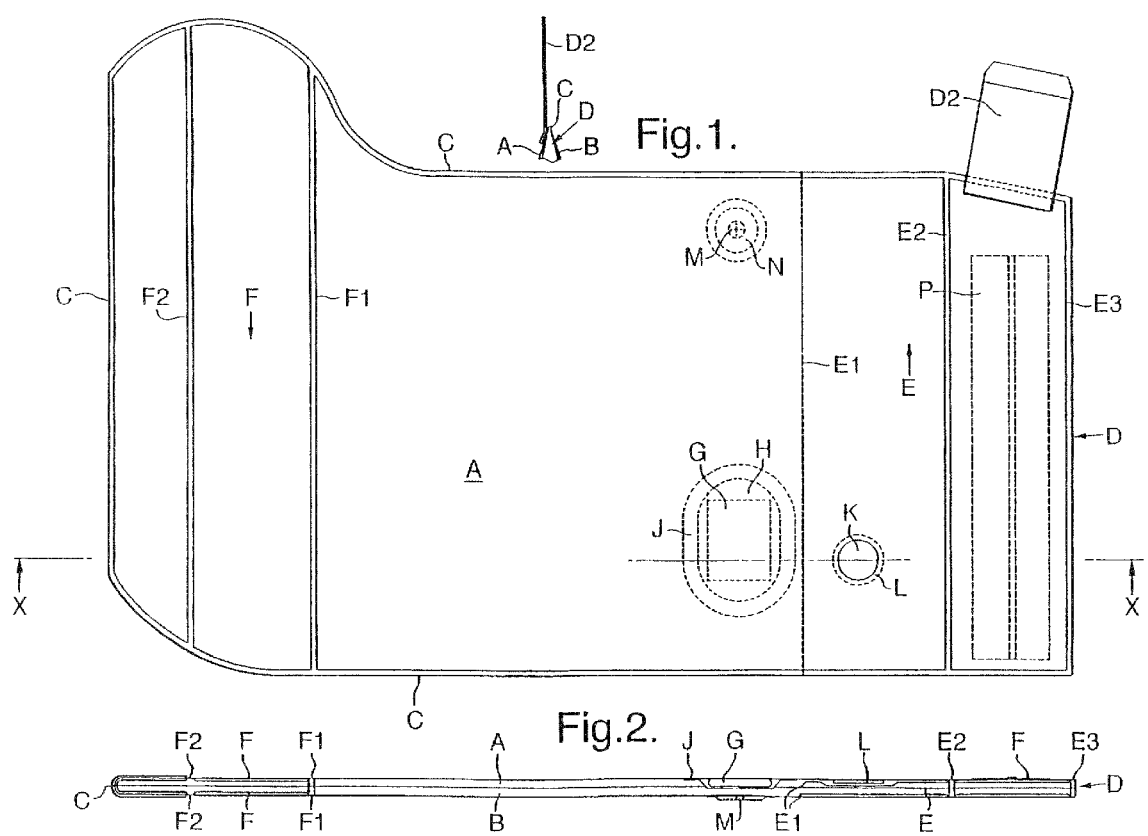

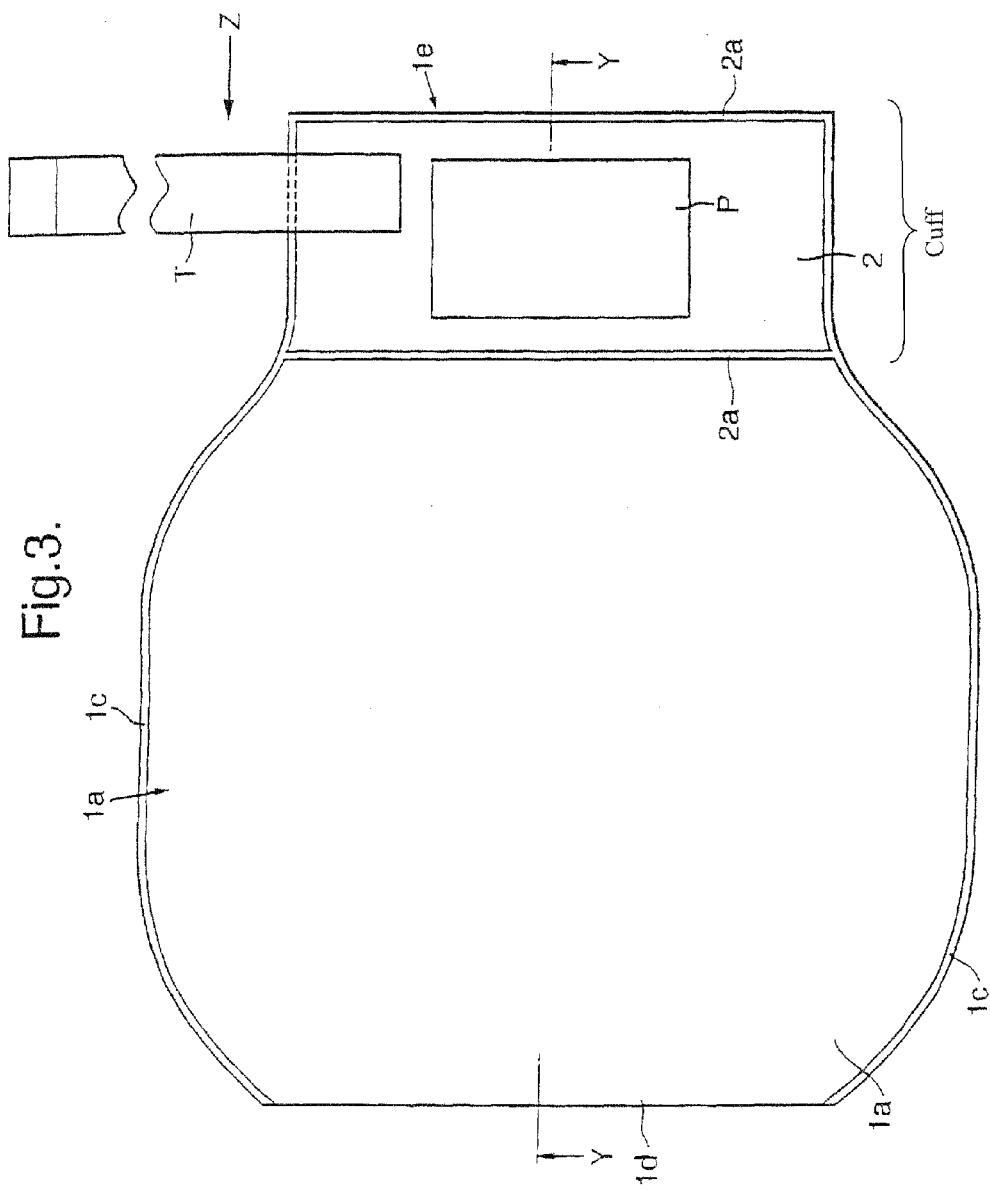

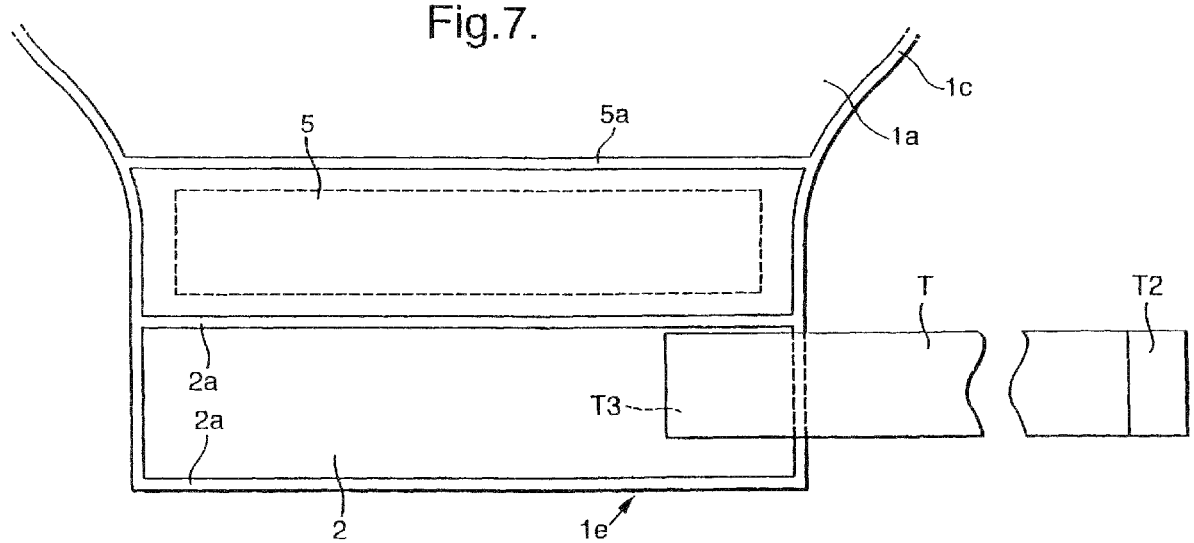

DEVICE FOR PROTECTING WOUNDS ON LIMBS

CROSS-REFERENCE TO EARLIER APPLICATION

This application is a continuation of co-pending U.S. application Ser. No. 11/265,941, filed Nov. 3, 2005; which is a continuation-in-part of U.S. application Ser. No. 09/889,940, filed Sep. 24, 2001 (now U.S. Pat. No. 6,982,358), which is a National Stage Application of International Application No. PCT/GB00/00208, filed Jan. 26, 2000; which claims priority to Great Britain Application No. 9901711.3, filed Jan. 26, 1999; Great Britain Application No. 9917445.0, filed Jul. 23, 1999; and Great Britain Application No. 9917443.5, filed Jul. 23, 1999, all of which are hereby incorporated in their entireties.

FIELD OF THE INVENTION

This invention relates to a device for the protection of wounds on the human body and is concerned primarily with a device for protecting open wounds, such as ulcers, burns or traumatised or gangrenous tissue, for example on the hands, lower limbs and the feet.

BACKGROUND OF THE INVENTION

In the United Kingdom at least, approx. 0.5 to 1% of the population at any one time suffers with venous and/or arterial ulceration affecting the lower limbs. Despite often vigorous treatments, either in hospital or by nurses in the community, leg ulcers may remain for several years. Often, even when healed, ulcers can recur and/or remain unhealed for many years. They also cause social problems, since the odour caused by infection is severe, and isolates the sufferer.

Typically, such a wound requires cleaning and dressing from twice daily to twice weekly, using expensive lotions and dressings, e.g. compression bandages, which often prove to have limited efficacy. The treatment is often very labour-intensive, in hospitals and even more so to the district nursing service.

In summary, the treatment of leg ulcers is expensive and often, has little or no effect. In addition, there are other types of wounds on limbs or stumps that require effective care. These include ulcers or wounds caused by diabetes, skin cancer or rheumatoid arthritis.

For example, a typical treatment for hand wounds and, in particular, burns is to clean the 'wound', then place the hand into a plastic bag and tip in either liquid paraffin or Flamazine (a topical antibiotic cream). In concept, the 'bag' protects the hand from trauma/secondary contamination, allows free movement of fingers ('auto-physiotherapy') and hence part-prevention of contractures, and allows visualisation of the hand. Often, a bag cannot easily be found, the medication cannot easily be found, and tape, to secure the bag, is wrapped so tightly that getting the bag off is difficult. Furthermore, all these same problems are encountered when the bag needs changing, especially if this is to be done in the home environment.

By way of example, an Accident & Emergency Department serving a catchment population of 180,000, sees between 1 and 3 persons per week having such hand wounds. Each requires once or twice daily dressings for an average of 10-12 days.

GB-A-2265314 discloses a protective article for securing around a body part, specifically an arm or leg. It comprises an inflatable protective shield formed from a breathable thermoplastic polyester urethane film, with a sealable cuff.

BRIEF SUMMARY OF THE INVENTION

According to the invention, a device comprises an enclosure of a plastics material, having an opening at one or both ends thereof with fastening means to enable the opening or openings to be closed around a limb (or stump) with an affected part contained within the enclosure, and including a fluid-absorbent material within the enclosure. Such a device can facilitate the protection (and potentially also healing), of wounds by providing a beneficial environment around the wound.

According to a preferred aspect of the invention, a device that may be fitted around the end of a limb comprises an enclosure generally defined by a gas-impermeable or, perhaps, water vapour-permeable plastic material, the enclosure having an opening with fastening means, to enable the opening to be closed around a limb with an affected part contained within the enclosure, and another part, e.g. the opposed end of the enclosure, having an internal lining of a fluid-absorbent material. An extra fluid-absorbent pad (or pads) may be positioned within and attached to the enclosure. An active filter (e.g. of charcoal) may be provided in association with means to vent gases through the wall of the enclosure and to reduce odours.

BRIEF DESCRIPTION OF THE DRAWINGS

The invention will now be described by way of example only with reference to the accompanying drawings. In the drawings:

FIG. 1 shows a wound-protecting boot embodying the invention, in flat form and in side elevation;

FIG. 2 shows the embodiment of FIG. 1 in section on X-X;

FIG. 3 shows a wound-protecting glove/sock embodying the invention, in flat form and in side elevation;

FIG. 7 shows the alternative cuff construction of FIG. 6 in section.

DETAILED DESCRIPTION OF THE INVENTION

Figure 4:
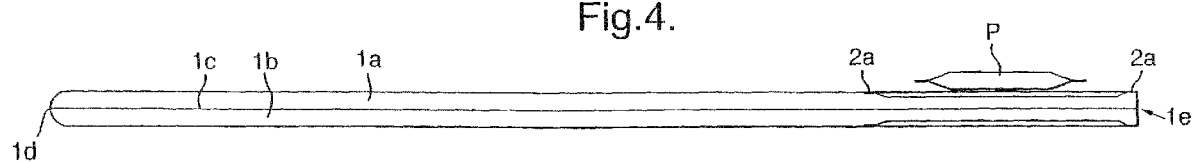
FIG. 4 shows the embodiment of FIG. 3 in section on Y-Y.

A device of this invention is intended to be applied around the end of limbs or limb stumps. For convenience, it may be described herein as a sleeve glove, sock or boot. In particular, a device intended to be fitted around a leg may be shaped as a sock or boot.

A device of the invention is intended for therapeutic use. It may be included within a sterile pack, for 'field' use.

The plastics material of the enclosure may comprise, for example, a 75 μm ethyl methyl acrylate film. Such material is pliable and has a soft feel, for patient comfort.

In a preferred embodiment, the plastic material of the enclosure comprises a multi-layered construction of plastics, e.g. 3, 5 or 7 layers. There may be one or more intermediate layers of polyvinylidene chloride (PVDC), ethylene-vinyl alcohol (EVOH) or other material that resists the passage of gas. The plastic material may include a layer which is absorbent to odours, especially for use with leg ulcers. Such materials are used in the food-packaging industry. The outer layers will conveniently be of ethylene-vinyl acetate (EVA) or low density polyethylene (LDPE); such materials allow the enclosure to be formed from two sheets which are welded around their peripheral edges. A different material may be used, which is water-vapour permeable, but still has anti-odour properties.

The enclosure may be opaque. Alternatively, it may be at least partially transparent, so that the wound is visible to the patient, nurse or physician. This is very practical in hospitals, since it avoids the need for the wound to be exposed on a consultant's visit, when that may not be otherwise considered necessary.

The absorbent lining material may be paper-based or, preferably, is of super-absorbent material. It is suitably attached to the enclosure by transverse weld lines. The opening in the enclosure may also include an internal absorbent lining, forming a "cuff". The fluid-absorbent material is provided in order to reduce the degree of excoriation of the limb part or stump, caused by the continual presence of water.

The fluid-absorbent pad(s) may be of a kind known for their super-absorbency. The active filter may comprise a charcoal material and may incorporate a valve adapted to relieve internal pressures that would otherwise cause ballooning of the enclosure.

The enclosure may also include a connection through which oxygen or other gases may be introduced into the enclosure. Hyperbaric oxygen is useful when a wound is infected by certain anaerobic organisms.

For use on the foot, the outer part of the enclosure opposite to the open end may have a reinforced part. More specifically, an external non-slip layer may be provided.

If desired, the device may include within, or have attached on to it, a capsule or pouch containing an agent such as liquid paraffin or Flamazine, and which may have a breakable seal, allowing release of the agent as required. Alternatively, an agent of this type may be applied when the device is changed.

A device according to this invention may be used to treat open wounds on the feet or legs of a body. For this purpose, the wound is first simply cleaned and the relevant limb enclosed within the device, to provide a substantially air-tight enclosure around the wound.

A device according to this invention can provide a warm and moist environment with adequate oxygenation, whilst maintaining the wound clean, without gross contamination occurring. The device is capable of containing odours. It can be tolerated by the patient who can be kept mobile (if appropriate) whilst wearing the device and avoiding aggravation of the condition.

The device is simple enough that, as necessary, it can be reapplied by the patient, perhaps more than once a day. However, it may be unnecessary to change the device so often, once again saving nursing care.

Figure 5:
FIG. 5 is a part view of the attachment tape viewed from Z in FIG. 3.
Figure 6:
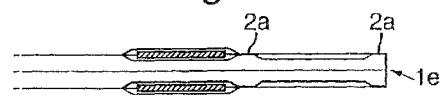
FIG. 6 shows an alternative arrangement for the cuff of the embodiment of FIG. 3.

The invention will now be described by way of example only with reference to the accompanying drawings. In the drawings:

FIG. 1 shows a wound-protecting boot embodying the invention, in flat form and in side elevation;

FIG. 2 shows the embodiment of FIG. 1 in section on X-X;

FIG. 3 shows a wound-protecting glove/sock embodying the invention, in flat form and in side elevation;

FIG. 4 shows the embodiment of FIG. 3 in section on Y-Y;

FIG. 5 is a part view of the attachment tape viewed from Z in FIG. 3;

FIG. 6 shows an alternative arrangement for the cuff of the embodiment of FIG. 3; and FIG. 7 shows the alternative cuff construction of FIG. 6 in section.

FIGS. 1 and 2 show a boot device for the protection and treatment of open wounds, and particularly for the protection and treatment of venous ulcerative disease of the lower limbs or gangrenous tissue. The boot is formed from two superimposed sheets of plastics material A and B, joined together by means of heat-sealing along edges C. The edges of the sheets are not sealed at the top end D which thus forms an opening for entry of a limb into the boot. In one construction, a single sheet is used with the side opposed to the end D folded over rather than being welded. The fold could, of course, be along another side.

The sheets each comprise a barrier film of the type which is used in the food packaging industry and for ostomy applications. Such films are generally multi-layered with a middle barrier layer being of, for example, a PVDC or a EVOH material. The sheets are mostly transparent, to allow the relevant area to be visually inspected.

The inner surfaces of the sheets A and B at the open end D include an absorbent layer E extending from the line E1 to the end D and secured by line welds E2 and E3. The end D may be fastened by pulling snugly around the limb and securing by means of a tab D2. This tab may have a peel-off paper layer covering an adhesive which can be pressed onto the outer surface of the boot, thus providing a snug fit around the limb.

The lower end of the boot has a similar lining F of comfortable, absorbent material on the inside surface. This lining extends between a securing weld F1 and the edge weld C, with an intermediate weld connection F2.

The inside surface of the boot includes a pad (or pads) of a super-absorbent material G retained by an overlaid porous paper membrane H and secured by a peripheral weld J. A small aperture K in the side is closed internally by a charcoal filter pad L which prevents the boot from ballooning and controls odour. A further aperture M in the side is closed by a rubber diaphragm N acting as a valve which permits oxygenation if required and by a suitable connection.

A reinforcing strip of plastics material P (also shown in FIGS. 3 and 4) is provided adjacent the top D. This strip may include identifying markings.

The transparent plastics enclosure allows the wound to be inspected. The enclosure provides a warm environment and retains moisture. Excessive moisture is absorbed by the pad material F in the foot part of the boot, and by the material E in the upper part.

Oxygenation may be enhanced by feed through the diaphragm N, and this may be particularly desirable for the treatment of anaerobic organisms. Odour is controlled by the charcoal filter L (which also permits the interior to breathe) as well as by the inherent odour-absorbing properties of the middle laminate layer of the plastics material.

In use, the boot will normally be changed on a once or twice daily basis, and the wound area cleaned using saline. The boot is then applied and secured by the adhesive tab(s) D2 around, for example, the leg. In hospital, this procedure may take up to 5 minutes of a nurse's time; conventional dressings for leg ulcers often take 20-30 minutes to change.

The construction permits the patient to change his or her own device, at home. It also allows the patient to be freely ambulatory, especially if the outer surface at the foot includes a non-slip coating or layer.

FIGS. 3 and 4 show a glove/sock device for the protection and treatment of open wounds and burns. The glove/sock is formed from two sheets of plastics material 1a and 1b joined together by means of heat-sealing or radio frequency-welding along the edges 1c. The edges of the sheets are not sealed at the (shaped) top and 1e which thus forms an opening for entry of a limb into the device. The other end 1d is formed by folding over the sheets which may then be formed from one piece.

As illustrated in FIGS. 3-5, the inner surfaces of the sheets at the open end 1e include a comfortable, absorbent paper layer 2 secured by line welds 2a. The end 1e may be fastened by pulling snugly around the limb and securing by means of a tab(s) T having a portion T3 attached to the cuff. The tab(s) T have a peel-off paper layer T1 removed by a pull-tab T2 and covering an adhesive which can be pressed onto the outer surface of the glove, thus providing a snug fit around the wrist.

As shown in FIGS. 6 and 7, the inside surface of the glove may include a partially or fully circumferential pad 5 of a super-absorbent material retained by an overlaid porous paper membrane and secured by a peripheral weld 5a.

Especially for the treatment of burns, the glove may include burstable sachets within the enclosure, containing Flamazine or any other suitable agent. Alternatively, sachets of such material, ready for use, may be attached to the outside of the glove.

In use, the glove will normally be changed on a regular basis and perhaps several times per day, and the affected area cleaned using saline. The glove/sock is then applied and secured by the adhesive tab(s) T around for example, the wrist. The mostly transparent, soft plastic allows the wound to be inspected. The plastic provides a warm environment and retains moisture, excessive moisture being (super-) absorbed by the pad material 5 and by the material 2.

Whether the invention is embodied by the relatively simple glove/sock of FIGS. 3-7 or by the boot of FIGS. 1-2, such devices are simple and economical to construct, and easy to use. They can readily be constructed in a range of different sizes.

Remarkably, devices of the invention may have a beneficial therapeutic effect. This has been demonstrated in the case of a leg ulcer that had been treated by conventional methods for several months; after this time, the wound remained unsightly and produced a disgusting odour. After just one week's usage of the boot illustrated in FIGS. 1-2, by the simple protocol described above, i.e. without dressings, both appearance and odour had improved; after another 10 days, infection had gone, and the wound had evidently started to heal.

More particularly, the boot has been used on 8 patients, one bilaterally, making a total of 9 legs. The mean age of the patients was 70 years (range 40-88 years). In 5 patients, the boot was used for one week. In two cases, it was discontinued after 3 days.

The aetiology of the ulcers was: 3 mixed arterio-venous, 1 secondary to pressure necrosis, 1 'trash foot' secondary to drug abuse, 1 venous and 2 arterial. 3 patients were diabetic. The length of time patients had had their ulcers ranged from 2 weeks to 6 years. Previous ulcer treatment had been simple dressings in all cases, Granuflex being used in 6 cases, jelonet in one and dry dressings in 1, all associated with additional gauze and crepe bandages.

The time taken to clean the ulcers ranged from 15 to 30 minutes per dressing change, which averaged 2 or 3 dressings per day. Wound swabs were taken in all cases. *Pseudomonas* was grown from 4 ulcers and *Staphylococcus aureus* from 3 limbs.

In each case, it took no more than 6 minutes to remove the boot, clean the ulcer and re-apply. There was an obvious improvement in 4 ulcers, with one limb becoming appropriate for application of a split skin graft (previously, the limb had been considered more likely to be amputated). In 2 cases, there was no discernible difference. The odour from infected ulcers was markedly improved in all cases.

5 patients said the boot was comfortable or very comfortable to wear, 2 said it was uncomfortable (one had boots bilaterally) and one patient was unable to comment due to medical health. Fluid collection was the only problem, and can be readily rectified by the provision of absorbent padding.

Since these results were obtained, several more patients have been successfully treated. It appears that a simple device has valuable utility.

The invention claimed is:

1. A method for improving healing in an arm having a wound wherein said method comprises using a device for improving healing of the wound on the arm, wherein said device comprises an enclosure comprising a gas impermeable plastic material, wherein said enclosure has a first end with a closeable opening and an adjustable fastener for substantially air-tight closing of the opening around a portion of the arm with the wound contained within said enclosure, wherein said device further comprises at least one fluid-absorbent material secured to aid enclosure wherein said fluid-absorbent material is secured to, and located only at, a closed end opposite said first end such that, when the device is applied to an arm with a wound, the closed end surrounds a hand or a stump of the arm, and, said fluid absorbent material is positioned within said enclosure at said closed end to absorb fluid produced by said wound, wherein said method comprises:

a. inserting the wounded arm into the closeable opening of the device;

b. placing the wounded arm in the enclosure so that the wound is contained within the enclosure; and c. securely closing the enclosure of the device about the wounded arm using the fastener creating a warm, moist environment within the enclosure thereby promoting wound healing.

2. The method, according to claim 1, wherein said device further comprises an odor-absorbent layer.

3. The method, according to claim 1, wherein said gas impermeable plastic material is pliable.

4. The method, according to claim 1, wherein said gas impermeable plastic material is at least partially transparent to provide visible access to the wound.

5. The method, according to claim 1, wherein said wound is an ulcer or is caused by diabetes, skin cancer, a burn, or rheumatoid arthritis.

6. The method, according to claim 1, wherein said device is in the shape of a glove.

* * * * *